United States Patent
Sankai et al.

(10) Patent No.: US 11,607,126 B2
(45) Date of Patent: Mar. 21, 2023

(54) ELECTRODES FOR BIOPOTENTIAL MEASUREMENT, BIOPOTENTIAL MEASURING APPARATUS, AND BIOPOTENTIAL MEASURING METHOD

(71) Applicants: University of Tsukuba, Ibaraki (JP); CYBERDYNE Inc., Ibaraki (JP)

(72) Inventors: Yoshiyuki Sankai, Ibaraki (JP); Alexsandr Igorevitch Ianov, Ibaraki (JP)

(73) Assignees: University of Tsukuba, Ibaraki (JP); CYBERDYNE Inc., Ibaraki (JP)

( * ) Notice: Subject to any disclaimer, the term of this patent is extended or adjusted under 35 U.S.C. 154(b) by 598 days.

(21) Appl. No.: 15/315,867

(22) PCT Filed: Jun. 1, 2015

(86) PCT No.: PCT/JP2015/065826
§ 371 (c)(1),
(2) Date: Mar. 6, 2017

(87) PCT Pub. No.: WO2015/186676
PCT Pub. Date: Dec. 10, 2015

(65) Prior Publication Data
US 2017/0188830 A1 Jul. 6, 2017

(30) Foreign Application Priority Data
Jun. 2, 2014 (JP) .............................. JP2014-114146

(51) Int. Cl.
*A61B 5/00* (2006.01)
*A61B 5/24* (2021.01)
(Continued)

(52) U.S. Cl.
CPC .............. *A61B 5/0006* (2013.01); *A61B 5/24* (2021.01); *A61B 5/2415* (2021.01); *A61B 5/25* (2021.01);
(Continued)

(58) Field of Classification Search
CPC ..... A61B 5/0006; A61B 5/04; A61B 5/04002; A61B 5/0408; A61B 5/0478; A61B 5/0492; A61B 5/0476
See application file for complete search history.

(56) References Cited

U.S. PATENT DOCUMENTS

2005/0215916 A1* 9/2005 Fadem ............... A61B 5/04004
600/544
2005/0277826 A1* 12/2005 Dunseath, Jr. ..... A61B 5/04004
600/410
2015/0109007 A1* 4/2015 Townsend ........... H03F 3/45179
324/692

FOREIGN PATENT DOCUMENTS

| JP | 2004-121360 A | 4/2004 |
| JP | 2012-120705 A | 6/2012 |
| JP | 2012-249645 A | 12/2012 |

OTHER PUBLICATIONS

Extended European Search Report for EP App No. 15803095.7 dated Dec. 12, 2017, 7 pgs.
(Continued)

*Primary Examiner* — Ronald Hupczey, Jr.
*Assistant Examiner* — Bradford C. Blaise
(74) *Attorney, Agent, or Firm* — Procopio, Cory, Hargreaves & Savitch LLP

(57) ABSTRACT

A biopotential can be measured with high accuracy without the electrodes coming into direct contact with the skin and without being affected by any motion artifact. The present invention comprises a first lead which detects a biopotential containing noise components, a second lead which is elec-
(Continued)

trically isolated from the first lead and detects noise components, and a differential amplifier circuit which is input with a first signal output from the first lead and a second signal output from the second lead, and which amplifies and outputs a difference between the first signal and the second signal, wherein a value of an input impedance on the second signal side of the differential amplifier circuit is set so that the noise components detected from the second lead will have a frequency that is higher than a frequency spectrum of the biopotential.

5 Claims, 6 Drawing Sheets

(51) Int. Cl.
    *A61B 5/25*     (2021.01)
    *A61B 5/30*     (2021.01)
    *A61B 5/291*     (2021.01)
    *A61B 5/296*     (2021.01)
    *A61B 5/369*     (2021.01)

(52) U.S. Cl.
    CPC ............... *A61B 5/291* (2021.01); *A61B 5/296* (2021.01); *A61B 5/30* (2021.01); *A61B 5/7225* (2013.01); *A61B 5/369* (2021.01); *A61B 5/6898* (2013.01); *A61B 5/7203* (2013.01); *A61B 2562/0214* (2013.01)

(56) References Cited

OTHER PUBLICATIONS

Ianov, A. I., et al., Development of Noise Resistant Hybrid Capacitive-Resistive Electrodes for Wearable Robotics Computing and Welfare, 2013 IEEE/RSJ International Conference on Intelligent Robots and Systems (IROS), Nov. 3-7, 2013, Tokyo, Japan, pp. 4249-4254.
International Search Report and Written Opinion for PCT App No. PCT/JP2015/065826 dated Aug. 25, 2015, 7 pgs.
Ianov, A. I., et al., Development of Hybrid Resistive-Capacitive Electrodes for Electroencephalograms and Electrooculograms, IEE Transactions on Sensors and Micromachines, 133(3), pp. 57-65, Mar. 1, 2013.

* cited by examiner

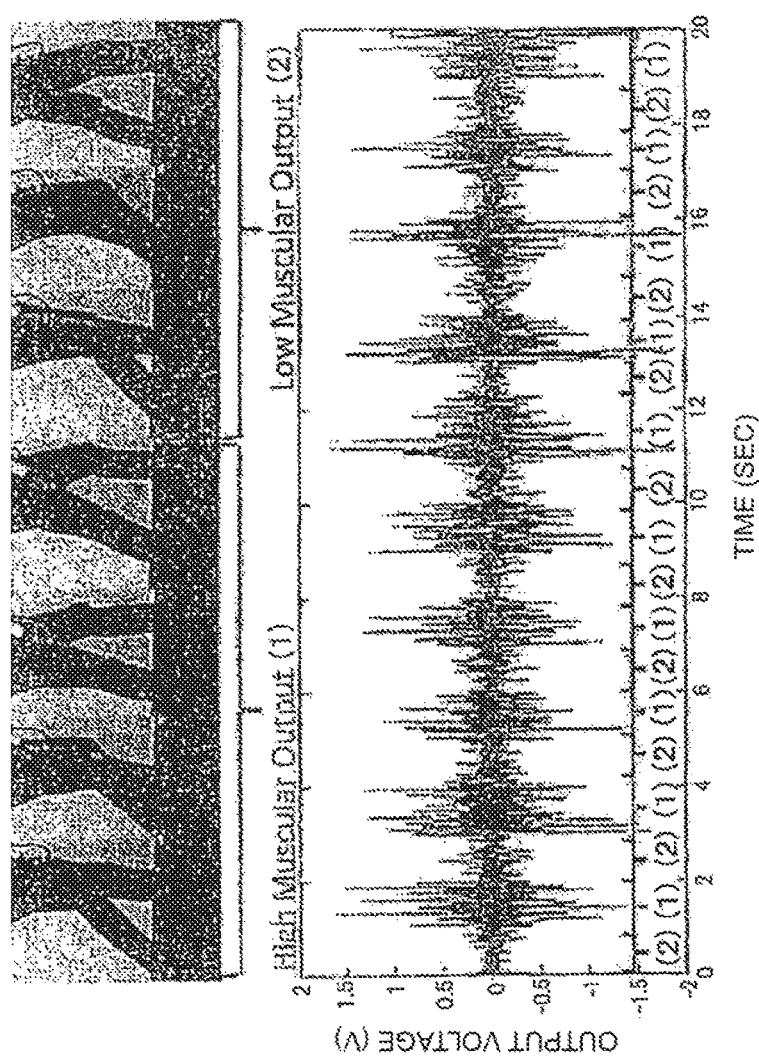

ELECTRODES FOR BIOPOTENTIAL MEASUREMENT, BIOPOTENTIAL MEASURING APPARATUS, AND BIOPOTENTIAL MEASURING METHOD

TECHNICAL FIELD

The present invention relates to a biopotential measuring electrode, a biopotential measuring apparatus, and a biopotential measuring method for measuring biological information by non-invasively placing electrodes on a living body.

BACKGROUND ART

Electrocardiograms (ECG), electroencephalograms (EEG), electrooculograms (EOG), electromyograms (EMG) and the like that are acquired by measuring biopotentials such as cardiac potentials, brain waves, ocular potentials, and myogenic potentials are important biological information in comprehending the condition of a trial subject/patient (hereinafter collectively referred to as "subject") in medical treatment.

Conventionally, the foregoing biopotentials were measured by causing electrodes to directly come into contact with the skin, or applying gel or the like on the skin and then causing electrodes to come into contact with the skin.

CITATION LIST

Patent Literature

PTL 1: Japanese Patent Application Publication No. 2012-120705
PTL 2: Japanese Patent Application Publication No. 2004-121360

SUMMARY OF THE INVENTION

Problems to be Solved by the Invention

Nevertheless, with the foregoing conventional measurement methods, there was a possibility that the skin would become irritated due to the application of gel. Furthermore, hair of the locations where the electrodes are to be placed needs to be shaved, and there was a problem in that biopotential measurement could not be easily performed.

Meanwhile, during biopotential measurement, undesired noise (hereinafter referred to as the "motion artifact") arises due to the movement of the subject, and there was a problem in that biopotentials could not be accurately measured because the waveform of the measurement result would be distorted due to the motion artifact.

The present invention was devised in view of the foregoing points, and an object of this invention is to provide a compact biopotential measuring electrode capable of accurately measuring a biopotential without coming into direct contact with the skin, as well as provide a biopotential measuring apparatus and a biopotential measuring method using the foregoing electrode.

Means to Solve the Problems

The biopotential measuring electrode according to one mode of the present invention comprises a first lead which detects a biopotential containing noise components, a second lead which is electrically isolated from the first lead and detects noise components, and a differential amplifier circuit which is input with a first signal output from the first lead and a second signal output from the second lead, and which amplifies and outputs a difference between the first signal and the second signal, wherein a value of an input impedance on the second signal side of the differential amplifier circuit is set so that the noise components detected from the second lead will have a frequency that is higher than a frequency spectrum of the biopotential.

In the biopotential measuring electrode according to one mode of the present invention, a value of an input impedance on the first signal side of the differential amplifier circuit is set so that the noise components of the signal output from the first lead are minimized.

The biopotential measuring electrode according to one mode of the present invention further comprises a first voltage follower circuit which is connected to one input end of the differential amplifier circuit and subjects the first signal to impedance conversion, and a second voltage follower circuit which is connected to another input end of the differential amplifier circuit and subjects the second signal to impedance conversion, wherein the value of the input impedance is set by replacing the input impedance on the second signal side of the differential amplifier circuit with the input impedance of the second voltage follower circuit.

In the foregoing biopotential measuring electrodes, the value of the input impedance is set by replacing the input impedance on the first signal side of the differential amplifier circuit with the input impedance of the first voltage follower circuit.

In the biopotential measuring electrode according to one mode of the present invention, the first lead is a circular electrode lead, and the second lead is a ring-shaped electrode lead, and disposed concentrically at a periphery of the first lead.

In the biopotential measuring electrode according to one mode of the present invention, the biopotential measuring electrode is configured by stacking, in order, a first layer which includes the first lead and the second lead, a second layer which is provided on the first layer and includes one substrate or a plurality of stacked substrates, and a third layer which is provided on the second layer and includes the differential amplifier circuit.

The biopotential measuring apparatus according to one mode of the present invention comprises a first electrode and a second electrode configured from the foregoing biopotential measuring electrode, an amplifier which amplifies and outputs a difference between an output of the first electrode and an output of the second electrode, a filter which performs filtering processing to an output signal of the amplifier, an A/D converter which A/D-coverts an output signal of the filter, and outputs a digital signal, and a transmission unit which transmits the digital signal.

In the biopotential measuring apparatus according to one mode of the present invention, the transmission unit transmits the digital signal via wireless transmission. Furthermore, in the biopotential measuring apparatus according to one mode of the present invention, the biopotential measuring apparatus is built into an electronic product worn or carried by a user.

The biopotential measuring method according to one mode of the present invention uses the foregoing biopotential measuring apparatus, and a biopotential is detected by causing the first electrode and the second electrode to face a skin of a subject without coming into contact with the skin of the subject (i.e., with clothing sandwiched therebetween).

Advantageous Effects of the Invention

According to the present invention, it is possible to accurately measure a biopotential without the electrodes coming into direct contact with the skin and without being affected by any motion artifact.

BRIEF DESCRIPTION OF DRAWINGS

FIG. 8 is a diagram showing a measurement result of the myogenic potential while walking.

DESCRIPTION OF EMBODIMENTS

An embodiment of the present invention is now explained with reference to the appended drawings.

Figure 1:
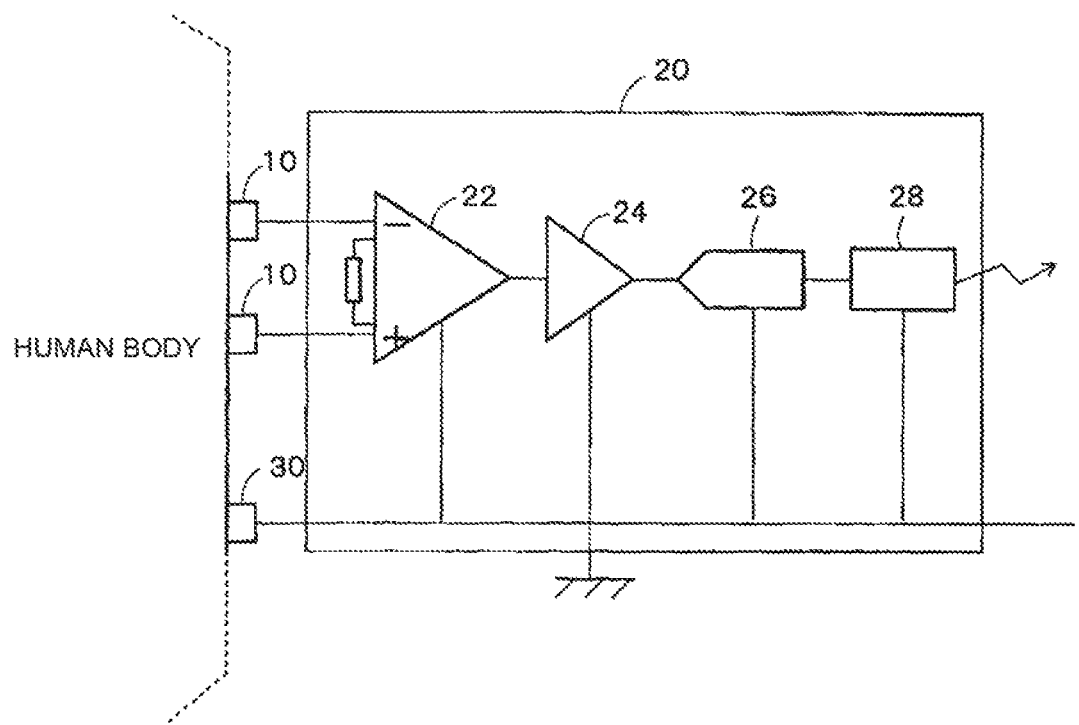
FIG. 1 is a schematic configuration diagram of the biopotential measuring apparatus according to this embodiment.

FIG. 1 is a schematic configuration diagram of the biopotential measuring apparatus according to an embodiment of the present invention. As shown in FIG. 1, the biopotential measuring apparatus comprises a pair of biopotential measuring electrodes 10, an arithmetic processing unit 20, and a ground electrode 30, and non-invasively measures an electric signal (biopotential signal) generated by a living body as a potential difference between two points on a surface (skin) of the human body.

The biopotential measuring electrodes 10 (hereinafter simply referred to as the "electrodes 10") are placed directly on the surface of a human body, or placed so as to face the human body surface via clothing or the like, detect biopotentials such as cardiac potentials, brain waves, ocular potentials, and myogenic potentials, and output the detected potentials to the arithmetic processing unit 20 via cables. The ground electrode 30 is used for obtaining a reference potential upon detecting the potential difference between two points.

The electrodes 10 form a capacitive coupling with the surface (skin) of a human body, and form a capacitive coupling with the ground electrode 30.

The arithmetic processing unit 20 includes an instrumentation amplifier 22, a filter 24, an A/D converter (analog/digital converter) 26, and a transmission unit 28. The instrumentation amplifier 22 is input with potentials output from the pair of electrodes 10, amplifies the difference between the two potentials, and outputs the amplified difference as a biopotential signal. The ground electrode 30 is connected to a reference potential terminal of the instrumentation amplifier 22.

The filter 24 is, for example, a band-pass filter, and performs filtering processing to the biopotential signal output from the instrumentation amplifier 22, and converts the biopotential signal into a signal that is suitable for the A/D conversion to be performed by the output-stage A/D converter 26.

The A/D converter 26 converts the analog signal output from the filter 24 into a digital signal. For example, the A/D conversion performed by the A/D converter 26 is based on a resolution of 16 bits and a sampling rate of 1 kHz. The transmission unit 28 transmits, via wireless transmission, the digital signal output from the A/D converter 26 to an analyzer not shown.

Figure 2:
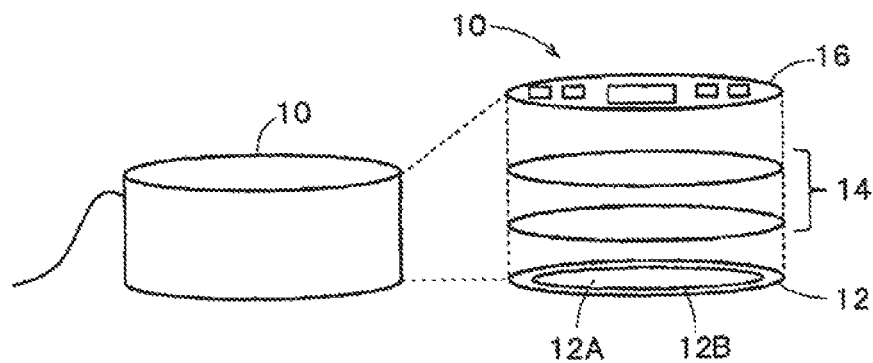
FIG. 2 is a schematic configuration diagram of the biopotential measuring electrode according to this embodiment.

FIG. 2 is a schematic configuration diagram of the electrode 10. As shown in FIG. 2, the electrode 10 comprises a stacked structure in which a solder layer 12, an intermediate layer 14, and a component layer 16 are stacked in order. The solder layer 12 is provided with two electrode leads on the same plane, namely; a lead (first lead) 12A for detecting a biopotential, and a lead (second lead) 12B for detecting non-white undesired noise.

When the distance between the electrodes and the human body surface is set up 3 mm as the maximum distance, the lead 12A is a circular electrode lead and has a diameter of 38 mm and a thickness of 1 mm, and the input impedance is set to 1 TΩ. Furthermore, the lead 12B is placed concentrically at the periphery of the lead 12A and has an external diameter of 40 mm and a thickness of 1 mm, and the input impedance is set to 1 MΩ. The lead 12B is covered with resin, and is electrically isolated from the lead 12A.

The input impedance of the lead 12B is set to be low at 1 MΩ, and, consequently, only noise having a frequency that is higher than the frequency spectrum of the biopotential signal is measured. As a result of electrically isolating the lead 12B from the lead 12A, the biopotential signal can be sufficiently measured even in a state where the contact area with the human body is small or the input impedance is low. In other words, the lead 12B can effectively eliminate, in the manner of a high-performance low-pass filter, only the signals having a frequency that is higher than the biopotential signal through filtering processing.

The intermediate layer 14 is a shield configured from one printed board or a plurality of stacked printed boards. The component layer 16 is provided with electronic components such as an amplifier described later and a circuit pattern. The leads 12A, 12B of the solder layer 12 and the electronic components and circuit pattern of the component layer 16 are connected via the intermediate layer 14.

Figure 3:
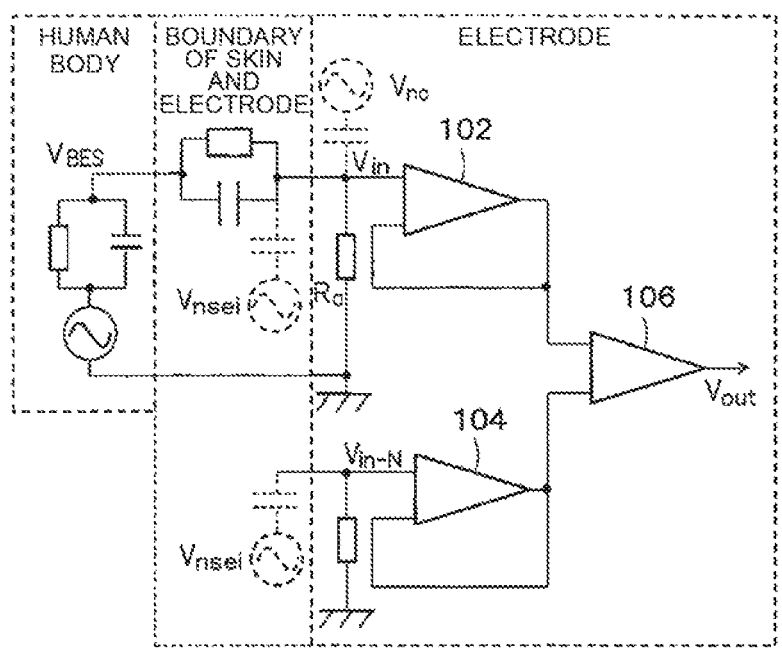
FIG. 3 is an equivalent circuit diagram upon mounting the biopotential measuring electrode according to this embodiment on a human body surface.

FIG. 3 shows an equivalent circuit diagram upon mounting the electrode 10 on the human body surface. When the biopotential signal including noise components detected by the lead 12A is $V_{in}$, and the noise components detected by the lead 12B are $V_{in\_N}$, the output signal $V_{out}$ of the electrode 10 can be represented with the following mathematical formula 1. The noise components $V_{in\_N}$ are configured only from motion artifacts that are generated from the vicinity of electronic products and non-white noise components such as pulse components.

[Math 1]

$$V_{out} = V_{in} - V_{in\_N} \quad (1)$$

The voltage follower circuit 102 which performs the impedance conversion of the signal $V_{in}$, the voltage follower circuit 104 which performs the impedance conversion of the noise components $V_{in\_N}$, and the differential amplifier circuit 106 which amplifies the difference between the output signal of the voltage follower circuit 102 and the output signal of the voltage follower circuit 104 and outputs the amplified difference as a signal $V_{out}$, are provided on the component layer 16.

When the voltage of the biopotential signal is $V_{BES}$, the total voltage of noise components at the boundary of the lead 12A and the skin is $V_{nsei}$, the total voltage of noise components in the lead 12A is $V_{nc}$, the impedance at the boundary of the lead 12A and the skin is $Z_{sei}$, the input impedance of the lead 12A is $R_c$, the noise impedance at the boundary of the lead 12A and the skin is $Z_{nsei}$, and the noise input impedance of the lead 12A is $Z_{nc}$, the signal $V_{in}$ can be represented with the following mathematical formula 2.

[Math 2]

$$V_{in} = \frac{R_c}{Z_{nc}} V_{nc} + \frac{R_c}{Z_{nsei}} V_{nsei} + \frac{R_c}{Z_{sei}} V_{BES} \quad (2)$$

Furthermore, the noise components of the signal $V_{in}$ can be minimized by optimizing the input impedance $R_c$ of the lead 12A based on the following mathematical formula 3. In the mathematical formula 3, $\varepsilon_o$ is the dielectric constant during a vacuum, $\varepsilon_r$ is the relative dielectric constant of the material, A is the detection area of the lead 12A near the skin, f is the frequency of the target signal, and d is the distance between the skin and the lead 12A.

[Math 3]

$$R_c = \frac{V_{in}}{V_{BES}} \cdot \frac{d}{\varepsilon_r \varepsilon_0 A 2\pi f} \quad (3)$$

With the differential amplifier circuit 106, the noise components of the signal $V_{in}$ are eliminated by the signal $V_{in\_N}$. Here, the value (for instance, foregoing 1 MΩ) of the input impedance $R_{c\_N}$ of the lead 12B is set so that the signal $V_{in\_N}$ as the noise components detected by the lead 12B will have a frequency that is higher than the frequency spectrum of the biopotential signal.

Accordingly, by providing the lead 12A for detecting a biopotential and the lead 12B for detecting noise, it is possible to eliminate frequency components that are higher than the biopotential signal; that is, it is possible to eliminate noise components. Accordingly, the electrode 10 can function as a high-order low-pass filter.

The signal that is output from the differential amplifier circuit 106 is a biopotential signal with reduced noise components, and this signal is input to the instrumentation amplifier 22 of the arithmetic processing unit 20.

It is also possible to equip the electrode 10 with a high-pass filter and eliminate the offset voltage that appears based on the potential difference between the two leads 12A, 12B. Furthermore, it is also possible to equip the leads 12A, 12B with a back-to-back diode, and inhibit the influence from the input bias current.

Power may be supplied to the electrode 10 from the arithmetic processing unit 20 via a cable, or the electrode 10 may be equipped with a built-in battery.

Example 1

Figure 4:
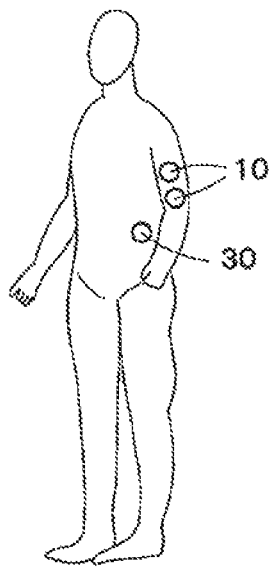
FIG. 4 is a diagram showing an example of mounting the biopotential measuring electrodes.
Figure 5A:
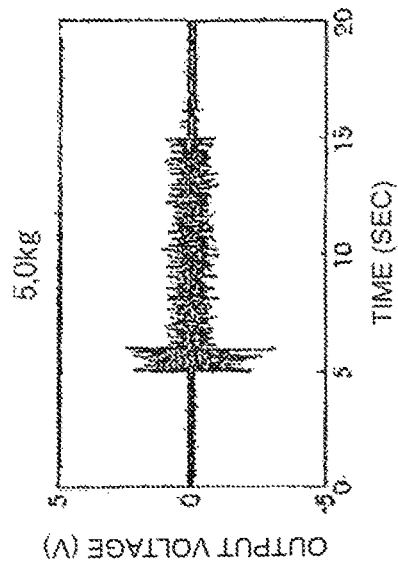
FIG. 5 is a diagram showing a measurement result of the myogenic potential upon raising and lowering the load.
Figure 5B:
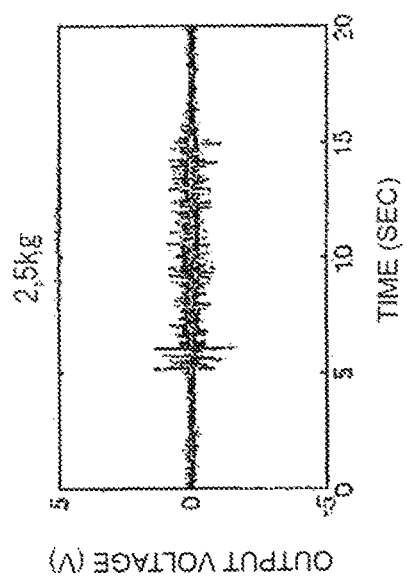
Figure 5C:
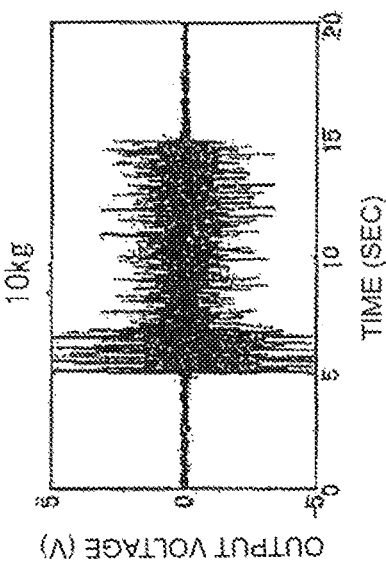
Figure 5D:
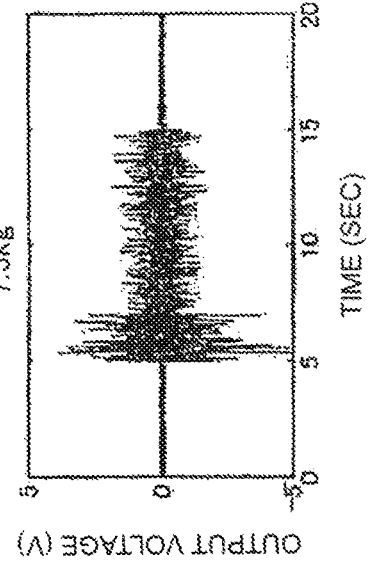

The biopotential measuring apparatus according to the foregoing embodiment was used to measure a myogenic potential upon raising and lowering an arm while holding a load. As shown in FIG. 4, a pair of electrodes 10 was placed at a part of the biceps brachii muscle, and the ground electrode 30 was placed at the abdominal region. Here, the subject was wearing a cotton shirt having a thickness of 1 mm, and the electrodes 10 were placed on the arm via the shirt.

Four types of loads of 2.5 kg, 5.0 kg, 7.5 kg, and 10.0 kg were used. In a state of holding the load, the arm was left lowered for 5 seconds, and the arm thereafter gradually raised the load for 5 seconds. Subsequently, the arm gradually lowered the load for 5 seconds, and the arm was thereafter left lowered for 5 seconds.

Here, as a result of detecting the noise spectrum in a 1 to 500 Hz band, the size of noise decreased pursuant to the increase in frequency, and the maximum value of the noise density appeared at a low-frequency band of 10 Hz or less, and was approximately 11 $\mu V/Hz^{1/2}$. Generally speaking, since the size of a myogenic potential is 100 to 1000 $\mu V$, it is evident that the biopotential measuring apparatus according to the foregoing embodiment is sufficiently reliable for measuring a myogenic potential.

The measurement results of the myogenic potential are shown in FIGS. 5(a) to 5(d). FIGS. 5(a) to 5(d) each show the measurement result in each case where the load was 2.5 kg, 5.0 kg, 7.5 kg, or 10.0 kg. In all measurement results, even during the period of 5 seconds to 15 seconds from the start; that is, even while the arm is being moved, no motion artifact was measured. Furthermore, during the period of 5 seconds to 7 seconds from the start; that is, when the movement of the arm was started, it was possible to measure a relatively large myogenic potential.

Subsequently, the electrodes 10 and the ground electrode 30 were placed at the same locations as FIG. 4, and a robot arm was controlled. As the robot arm, JACO manufactured by Kinova Robotics was used. The arm was motionless for 10 seconds from the start of measurement, and the arm (elbow) was bent 45° and returned for 10 seconds after 10 seconds lapsed from the start of measurement, and this was repeated twice.

Figure 6:
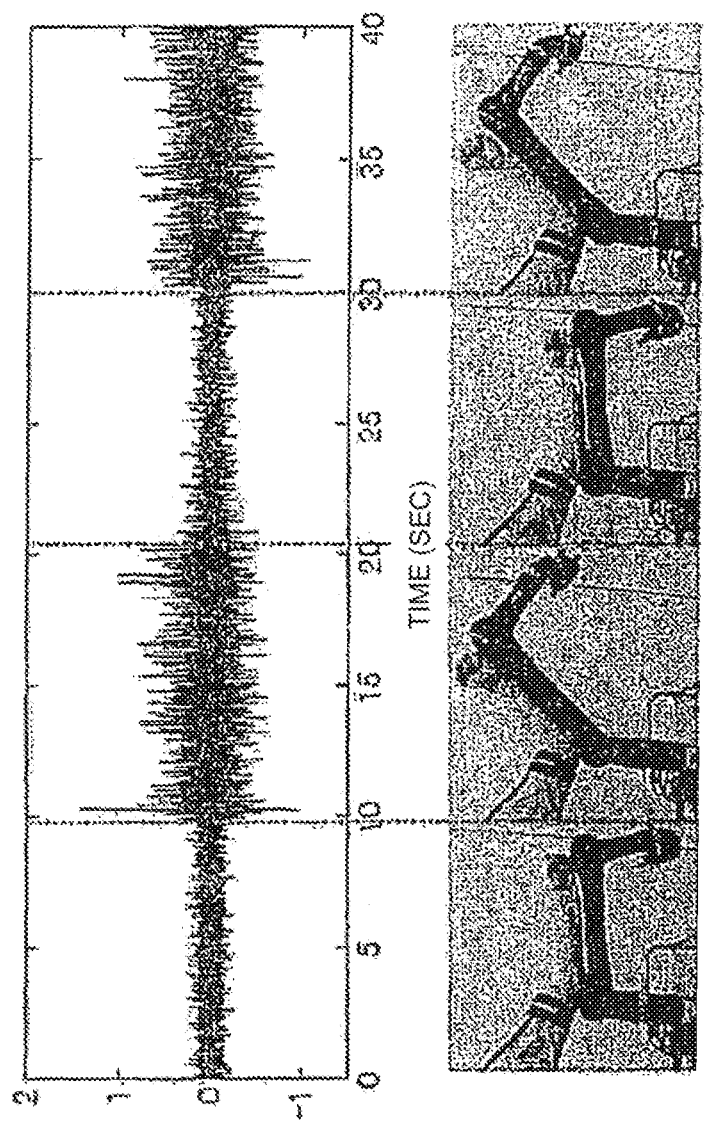
FIG. 6 is a diagram showing a measurement result of the myogenic potential upon controlling the robot arm.

The measurement result of the myogenic potential is shown in FIG. 6. Note that, as shown in FIG. 6, the myogenic potential was measured while causing the subjects arm to be contact with the robot arm. Based on the measurement result, it is evident that the biceps brachii muscle is stimulated based on the arm weight, and a signal that is sufficiently strong for use as a simple trigger algorithm can be generated. Furthermore, it is evident that a motor of the robot arm near the electrode 10 does not interfere with the measurement of the myogenic potential.

Figure 7:
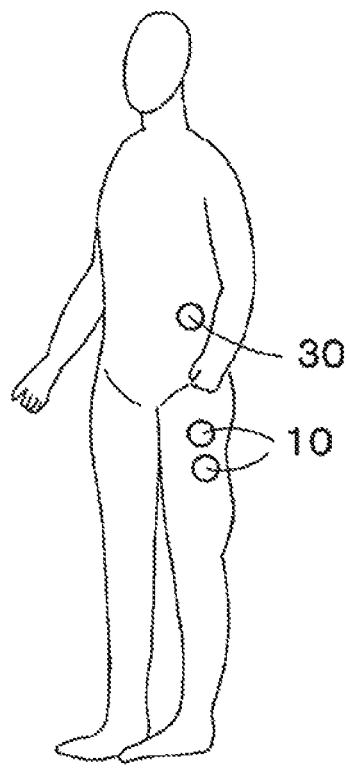
FIG. 7 is a diagram showing an example of mounting the biopotential measuring electrodes.

Subsequently, the myogenic potential while walking was measured. As shown in FIG. 7, a pair of electrodes 10 was placed at a part of the quadriceps femoris muscle, and the ground electrode 30 was placed at the abdominal region. Here, the subject was wearing jeans having a thickness of 2.2 mm, and the electrodes 10 were placed on the leg via the jeans. The subject walked on a treadmill for 20 seconds at a speed of 1.2 m/s.

The measurement result of the myogenic potential is shown in FIG. 8. In a single stance phase of advancing the trunk while supporting the body weight with one leg, it is evident that the myogenic potential increases. The myogenic potential in a swing phase of bending the knees and the hip joint and thereafter extending the same to swing the leg forward or in a double stance phase of supporting the body weight with both legs decreases in comparison to the myogenic potential in the single stance phase. Furthermore, no motion artifact was measured.

Accordingly, by using the biopotential measuring apparatus according to this embodiment, it is possible to measure the myogenic potential, even from above the clothing, while suppressing the noise level to 11 $\mu V/Hz^{1/2}$. Furthermore, it is also possible to measure the myogenic potential even in a state where an electronic component is located near the electrodes 10.

The electrodes 10 of the biopotential measuring apparatus according to this embodiment are internally equipped with two leads; namely, a lead 12A for detecting a biopotential (including noise) and a lead 12B for detecting noise, and a differential amplifier circuit 106 for outputting the difference between the detection signals of the two leads.

Here, the value of the input impedance of the lead 12B is set so that, among the noise components detected by the lead 12B, only the noise components having a frequency that is higher than the frequency spectrum of the biopotential are measured. Furthermore, the value of the input impedance of the lead 12A is optimized so that the noise components of the biopotential signal output from the lead 12A are minimized.

Consequently, it is possible to eliminate noise components from the signals provided by the electrodes 10 to the arithmetic processing unit 20, and a biopotential can be accurately measured, even from above clothing, without the electrodes 10 coming into direct contact with the skin. Accordingly, biopotential measurement can be performed easily.

Example 2

The biopotential measuring apparatus according to the foregoing embodiment may also be built into an electronic product such as a wearable device, a wrist watch or a mobile phone which is worn or carried by the user and used near the individual. In the foregoing case, the biopotential measuring apparatus configures a part of the function of the electronic product. As a result of the user wearing the electronic product or carrying the electronic product in one's pocket, the biopotential measuring electrodes of the present invention are placed to face the human body surface of the user, and a biopotential can thereby be measured accurately. Accordingly, biopotential measurement can be performed easily.

Note that the present invention is not limited to the foregoing embodiments, and the constituent elements may be modified and embodied to an extent that does not deviate from the subject matter thereof at the stage of implementation. Furthermore, various inventions can be devised based on the appropriate combination of the plurality of constituent elements disclosed in the foregoing embodiments. For example, certain constituent elements may be deleted from all constituent elements disclosed in the embodiments. In addition, constituent elements across different embodiments may be suitably combined.

REFERENCE SIGNS LIST

10: Biopotential measuring electrode
12A, 12: Lead
14: Intermediate layer
16: Component layer
20: Arithmetic processing unit
22: Instrumentation amplifier
24: Filter
26: A/D converter
28: Transmission unit
30: Ground electrode

The invention claimed is:
1. A biopotential measuring electrode, the biopotential measuring electrode comprises comprising:
an electrode having a stacked structure obtained by stacking, in a following order:
a first layer having a first lead configured from a circular electrode lead, and a second lead, electrically isolated from the first lead, the second lead being configured as a ring-shaped electrode lead concentrically located at a periphery of the first lead and located on a same plane as the first lead;
a second layer provided on the first layer, and which includes one substrate; and
a third layer provided on the second layer and which includes a differential amplifier circuit that receives a first signal including both a biopotential signal and noise components output from the first lead and a second signal including noise components output from the second lead, and the differential amplifier circuit is configured to amplify and output a difference between the first signal and the second signal,
wherein the first layer, the second layer, and the third layer are sequentially stacked;
wherein, the electrode is configured to detect the biopotential signal by being placed opposite a skin of a subject with clothing interposed between the electrode and the skin so that the electrode does not contact the skin of the subject without being positioned to contact the skin of the subject such that clothing is sandwiched between the electrode and the skin of the subject,
wherein a value $R_c$ of an input impedance on a first signal side of the differential amplifier circuit is represented with following mathematical formula (1) when a voltage of the first signal output from the first lead, which includes the biopotential signal and the noise components, is $V_{in}$, a voltage of the biopotential signal without the noise components output from the first lead is $V_{BES}$, a dielectric constant during a vacuum is $\varepsilon_o$, a relative dielectric constant of the clothing is $\varepsilon_r$, a detection area of the first lead near the skin is A, a frequency of the biopotential signal is f, and a distance between the skin and the first lead is d:

$$R_c = \frac{V_{in}}{V_{BES}} \cdot \frac{d}{\varepsilon_r \varepsilon_o A 2\pi f} \qquad (1)$$

wherein the value $R_c$ of the input impedance on the first signal side is optimized so that the noise components of the first signal are minimized based on the mathematical formula (1), and
wherein a value of an input impedance on a second signal side of the differential amplifier circuit is set so that the noise components detected from the second lead will have a frequency that is higher than a frequency spectrum of the biopotential signal,
wherein the voltage of the first signal output from the first lead yin is represented by the mathematical formula (2) providing:

$$V_{in} = \frac{R_c}{Z_{nc}} V_{nc} + \frac{R_c}{Z_{nsei}} V_{nsei} + \frac{R_c}{Z_{sei}} V_{BES} \qquad (2)$$

wherein Vnc is a total voltage of noise components in the first lead, $V_{BES}$ is the voltage of the biopotential signal, $V_{nsei}$ is a total voltage of noise components at a boundary of the first lead and the skin, $Z_{sei}$ is the impedance at the boundary of the first lead and the skin, $R_c$ is the input impedance of the first lead, $Z_{nsei}$ is the noise impedance at the boundary of the first lead and the skin, and $Z_c$ is the noise input impedance of the first lead, and wherein the second lead is coated with a resin configured to reduce impedance relative to the first lead.

2. The biopotential measuring electrode according to claim 1, further comprising:
   a first voltage follower circuit which is connected to one input end of the differential amplifier circuit and subjects the first signal to impedance conversion; and
   a second voltage follower circuit which is connected to another input end of the differential amplifier circuit and subjects the second signal to impedance conversion,
   wherein the value of the input impedance on the first signal side of the differential amplifier circuit is set by replacing the input impedance on the first signal side of the differential amplifier circuit with an input impedance of the first voltage follower circuit, and
   wherein the value of the input impedance on the second signal side of the differential amplifier circuit is set by replacing the input impedance on the second signal side of the differential amplifier circuit with an input impedance of the second voltage follower circuit.

3. A biopotential measuring apparatus, comprising:
   a first electrode and a second electrode, wherein at least one of the first electrode and the second electrode is a biopotential measuring electrode according to claim 1;
   an amplifier which amplifies and outputs a difference between an output of the first electrode and an output of the second electrode;
   a filter which performs filtering processing to an output signal of the amplifier;
   an A/D converter which A/D converts the filtered output signal from the filter, and outputs a digital signal; and
   a transmission unit which transmits the digital signal.

4. The biopotential measuring apparatus according to claim 3,
   wherein the transmission unit transmits the digital signal via wireless transmission.

5. The biopotential measuring apparatus according to claim 3,
   wherein the biopotential measuring apparatus is built into an electronic product worn or carried by a user.

* * * * *